[54] ANTIMICROBIAL DERIVATIVES OF 3-(1H-IMIDAZOL-1-yl)-2-PROPEN-1-ONES

[75] Inventor: Hans Hoehn, Tegernheim, Fed. Rep. of Germany

[73] Assignee: E. R. Squibb & Sons, Inc., Princeton, N.J.

[21] Appl. No.: 224,242

[22] Filed: Jan. 12, 1981

Related U.S. Application Data

[63] Continuation of Ser. No. 117,139, Jan. 30, 1980, Pat. No. 4,273,776.

[51] Int. Cl.³ .......................................... A61K 31/415
[52] U.S. Cl. ............................... 424/273 R; 424/263; 542/440; 548/341
[58] Field of Search ....................... 548/341; 542/440; 424/263, 273 R

[56] References Cited

U.S. PATENT DOCUMENTS 3,929,819  12/1975  Inazuka et al. ................. 542/440 X
4,067,989   1/1978  Shephard et al. .............. 542/440 X

OTHER PUBLICATIONS

Chemical Abstracts, 67:32647r (1967) Hoffmann, S., et al., *Z. Chem.*, 7(1), 12(1967).
Chemical Abstracts, 56:11996b (1962) Schonbaum, G., et al., *J. Biol. Chem.*, 236, 2930-2935 (1961).

*Primary Examiner*—Richard A. Schwartz
*Attorney, Agent, or Firm*—Lawrence S. Levinson; Burton Rodney

[57] ABSTRACT

Compounds are provided having the structure

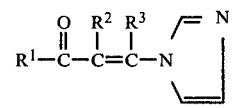

wherein
$R^1$ is lower alkyl; phenyl-lower alkyl; phenyl; substituted phenyl wherein the phenyl group bears one or two halogen, hydroxy, lower alkyl, lower alkoxy, lower alkylthio, cyano or nitro groups; 5- or 6-membered monocyclic aromatic heterocyclics containing one hetero atom, namely, O, S or N, such as furanyl, pyridinyl or thiophenyl; and substituted heterocyclics wherein any of the above heterocyclics bears one halogen, hydroxy, lower alkyl, lower alkoxy, lower alkylthio, cyano or nitro group;
$R^2$ and $R^3$ may be the same or different and each may be hydrogen, lower alkyl, halogen, phenyl, or substituted phenyl wherein the phenyl group bears one halogen, hydroxy, lower alkyl, lower alkoxy, lower alkylthio, cyano or nitro group.

The above compounds as well as acid-addition salts thereof are useful as antimicrobial agents.

4 Claims, No Drawings

ANTIMICROBIAL DERIVATIVES OF 3-(1H-IMIDAZOL-1-yl)-2-PROPEN-1-ONES

REFERENCE TO OTHER APPLICATIONS

This application is a continuation of application Ser. No. 117,139, filed Jan. 30, 1980, now U.S. Pat. No. 4,273,776.

SUMMARY OF THE INVENTION

This invention relates to new derivatives of 3-(1H-imidazol-1-yl)-2-propen-1-ones and the acid-addition salts of these compounds. These new compounds have the general formula

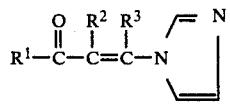

The symbols $R^1$ to $R^3$ have the following meaning in formula I and throughout the specification:

$R^1$ is lower alkyl; phenyl lower alkyl; phenyl; substituted phenyl wherein the phenyl group bears one or two halogen, hydroxy, lower alkyl, lower alkoxy, lower alkylthio, cyano or nitro groups; monocyclic aromatic heterocyclic; or substituted monocyclic aromatic heterocyclic wherein the heterocyclic bears one halogen, hydroxy, lower alkylthio, lower alkoxy, cyano or nitro group; $R^2$ and $R^3$ may be the same or different and are hydrogen, lower alkyl, halogen, phenyl or substituted phenyl wherein the phenyl group bears one halogen, hydroxy, lower alkyl, lower alkylthio, lower alkoxy, cyano or nitro group.

The new compounds of formula I are useful as antimicrobial agents, especially against fungi strains.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$-$C_4$, especially $C_1$-$C_2$, lower alkyl groups are preferred.

The halogens are the four common halogens, chlorine and bromine being preferred in that order. Preferably, but not necessarily, all halogens in a single compound are the same.

The term "monocyclic aromatic heterocyclic" as used herein includes mono hetero 5- or 6-membered rings containing one hetero atom, namely, O, S, or N, such as furan, pyridine and thiophene.

Preferred embodiments of this invention are compounds of formula I wherein $R^1$ is substituted phenyl, such as halophenyl or dihalophenyl, such as 2,4-dichlorophenyl, $R^2$ is hydrogen, lower alkyl, such as methyl or ethyl, or halogen, such as chloro, and $R^3$ is hydrogen or lower alkyl, such as methyl or ethyl, and the hydrohalide salts, such as hydrochloride salts thereof.

The new compounds of formula I are formed by the following series of reactions.

A ketone of the formula

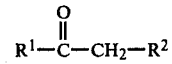

is made to react with esters of formula

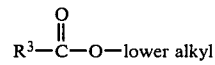

at room or elevated temperature in the presence of a condensing agent, e.g., sodium hydride, sodium wire, metal alcoholate and the like. The resulting compound of the formula

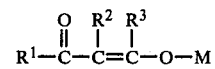

in which M represents metals like sodium, potassium or the like, is neutralized and then reacted with an imidazole of the formula

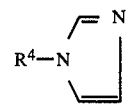

in which $R^4$ denotes hydrogen, metals like sodium, potassium or the like, or carbonylimidazole or thionylimidazole, to give compounds of formula I.

A preferred method for preparing products of formula I is the reaction of the hydroxymethylene compound of formula IV (M=H) (prepared in accordance with R. Gupta et al, Indian J. Chem., Vol. 15B, 642 (1977)) with the carbonyl-bis-imidazole or the thionyl-bis-imidazole of the formula

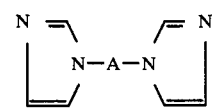

wherein A represents —CO— or —SO—.

The compounds of formula I form salts which are also part of this invention. The salts include acid-addition salts, particularly the non-toxic, physiologically acceptable members. The bases of formula I form salts by reactions with one or more equivalents of any of a variety of the common inorganic and organic acids providing acid-addition salts including for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid-addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base, such as barium hydroxide or sodium hydroxide, to obtain the free base of formula I. Other salts may then be formed from the free base by reaction with one or more equivalents of acid containing the desired acid group.

The new compounds of formula I and their salts are useful as anti-fungal and anti-bacterial agents and may be used to combat infections in various mammalian species, such as mice, rats, dogs, guinea pigs and the like, particularly those due to organisms such as *Candida albicans*, as well as organisms such as *Trichomonas vaginalis* or *Trichophyton mentagrophytes*. For example, a compound or mixture of compounds of formula I or physiologically acceptable acid-addition salt thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following Examples represent preferred embodiments of the invention. Temperatures are on the Celsuis scale.

EXAMPLE 1

1-(2,4-Dichlorophenyl)-3-(1H-imidazol-1-yl)-2-propen-1-one

A. 1-(2,4-Dichlorophenyl)-3-hydroxy-2-propen-1-one

The above starting material is prepared according to R. Gupta et al., Indian J. Chem., Vol., 15B, 642 (1977), m.p. 62°–63°.

B. 1-(2,4-Dichlorophenyl)-3-(1H-imidazol)-1-yl)-2-propen-1-one 2.2 g of 1-(2,4-Dichlorophenyl)-3-hydroxy-2-propen-1-one (0.01 mol) are dissolved in 50 ml of dry benzene. While stirring 3.2 g of carbonyl-bis-imidazole (0.02 mol) are added and the reaction mixture is warmed to about 50°–70° for a short time to get the components dissolved. If required the solution is filtered clear and then allowed to stand at room temperature for 22 hours. The crystallized product is filtered off, washed with petroleum ether (40°–60°) and dried (1.8 g). Treatment with water and drying in a desiccator over $P_2O_5$ furnished 1.5 g of 1-(2,4-dichlorophenyl)-3-(1H-imidazol-1-yl)-2-propen-1-one, which after recrystallization from ethyl acetate melts at 160°–162°.

Addition of petroleum ether (40°–60°) to the benzene mother liquor and work up in the foregoing manner gives an additional crop of 0.7 g. Total yield 2.2 g (82%).

EXAMPLE 2

1-(2,4-Dichlorophenyl)-3-(1H-imidazol-1-yl)-2-methyl-2-propen-1-one

A. 1-(2,4-Dichlorophenyl)-3-hydroxy-2-methyl-2-propen-1-one

The above starting material is prepared using the literature method mentioned in Example 1A; the so-prepared starting material melts at 131°–132°.

B. 1-(2,4-Dichlorophenyl)-3-(1H-imidazol-1-yl)-2-methyl-2-propen-1-one

Following the procedure according to Example 1B, except reacting 1-(2,4-dichlorophenyl)-3-hydroxy-2-methyl-2-propen-1-one with carbonyl-bis-imidazole, the title compound is produced, m.p. 129°–130° (ethanol/refrigerator), yield 79%.

EXAMPLE 3

1-(2,4-Dichlorophenyl)-3-(1H-imidazol)-1-yl)-2-buten-1-one, hydrochloride, hydrate (1:1:1)

A. 1-(2,4-Dichlorophenyl)-3-hydroxy-2-buten-1-one

The above starting material is prepared according to the literature method of Example 1A; m.p. 44°–46°.

B. 1-(2,4-Dichlorophenyl)-3-(1H-imidazol-1-yl)-2-buten-1-one, hydrochloride, hydrate (1:1:1)

9.2 g of 1-(2,4-dichlorophenyl)-3-hydroxy-2-buten-1-one (0.04 mol) are dissolved in 150 ml of dry benzene. While stirring 13 g of carbonyl-bis-imidazole (0.08 mol) are added and the reaction mixture is warmed to about 75° for a short time to get the carbonyl-bis-imidazole dissolved. The clear solution is allowed to stand overnight. Then the solvent is removed in vacuo and the residual product, after treatment with water, is taken up with ether. The ethereal extract is twice shaken with water, dried with sodium sulfate, charcoaled, filtered and, while stirring, ethereal hydrochloric acid is added to precipitate the hydrochloride of the title compound. The filtered off product is washed with ethyl acetate/ether and recrystallized from ethyl acetate/absolute alcohol (3:1); yield 5.4 g (40.3%), m.p. 124°–126°.

EXAMPLE 4

2-Chloro-1-(2,4-dichlorophenyl)-3-(1H-imidazol-1-yl)-2-propen-1-one

A. 2-Chloro-1-(2,4-dichlorophenyl)-3-hydroxy-2-propen-1-one

The above starting material is prepared according to the literature method of Example 1A by reacting 2-chloro-1-(2,4-dichlorophenyl)-ethan-1-one with ethyl formate, m.p. 162°.

B. 2-Chloro-1-(2,4-dichlorophenyl)-3-(1H-imidazol-1-yl)-2-propen-1-one 10 g of 2-chloro-1-(2,4-dichlorophenyl)-3-hydroxy-2-propen-1-one (0.04 mol) are dissolved in 175 ml of dry benzene. While stirring, 13 g of carbonyl-bis-imidazole (0.08 mol) are added and the reaction mixture is refluxed shortly to get a clear solution. After standing for 24 hours the solvent is removed in vacuo, the residual product is treated with 150 ml of water, filtered off, washed again with water and dried in a desiccator over $P_2O_5$. Yield 11 g (91%), m.p. 149°–151°. Recrystallization from ethyl acetate elevates the melting point of the title compound to 150°–152°.

EXAMPLE 5

1-(2,4-Dichlorophenyl)-3-(1H-imidazol-1-yl)-2-ethyl-2-propen-1-one, hydrochloride, hydrate (2:2:1)

A.

1-(2,4-Dichlorophenyl)-3-hydroxy-2-ethyl-2-propen-1-one

The above starting material is prepared following the procedure of Example 1A, m.p. 117°–119°.

B.

1-(2,4-Dichlorophenyl)-3-(1H-imidazol-1-yl)-2-ethyl-2-propen-1-one hydrochloride, hydrate (2:2:1)

Following the procedure according to the method of Example 3B, except reacting 1-(2,4-dichlorophenyl)-3-hydroxy-2-ethyl-2-propen-1-one with carbonyl-bis-imidazole, the title compound is produced, m.p. 101°–103°, yield 46%.

EXAMPLES 6 TO 22

The following additional products of formula C are obtained by the procedure of Example 1 by employing as starting materials the compounds of formula A and of formula B set out below.

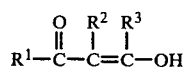

A

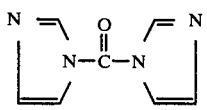

B

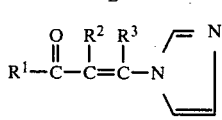

C

| Ex. No. | R¹ | R² | R³ |
|---|---|---|---|
| 6. | CH₃ | H | H |
| 7. | C₂H₅ | C₂H₅ | o-OHC₆H₄ |
| 8. | C₆H₅ | H | o-CH₃C₆H₄ |
| 9. | C₆H₅CH₂ | C₆H₅CH₂ | H |
| 10. | C₃H₇ | CH₃ | o-CH₃OC₆H₄ |
| 11. | p-OHC₆H₄ | Cl | CH₃ |
| 12. | furyl (O) | CH₃ | CH₃ |
| 13. | o-CH₃C₆H₄ | H | o-BrC₆H₄ |
| 14. | C₆H₅ | C₆H₅ | H |

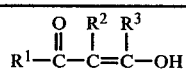

A

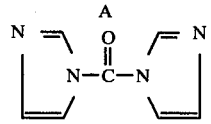

B

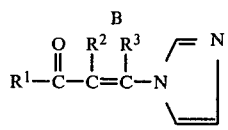

C

| Ex. No. | R¹ | R² | R³ |
|---|---|---|---|
| 15. | thienyl (S) | C₆H₅ | o-ClC₆H₄ |
| 16. | p-CH₃SC₆H₄ | H | Cl |
| 17. | m-NO₂C₆H₄ | Br | H |
| 18. | pyridyl (N) | p-CNC₆H₄ | o-ClC₆H₄ |
| 19. | furyl (O) | C₃H₇ | p-CH₃SC₆H₄ |
| 20. | 2-methylthienyl | C₂H₅ | o-OHC₆H₄ |
| 21. | C₆H₅ | H | CH₃ |
| 22. | cyanopyridyl | m-NO₂C₆H₄ | H |

What is claimed is:

1. A method for treating infections in mammals caused by Trichomonas vaginalis which comprises administering to a mammalian host an effective amount of a compound of the formula

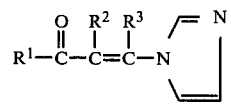

wherein
R¹ is lower alkyl; phenyl-lower alkyl; phenyl; substituted phenyl wherein the phenyl group bears one or two halogen, hydroxy, lower alkyl, lower alkoxy, lower alkylthio, cyano or nitro groups; 5- or 6-membered monocyclic aromatic heterocyclic containing one O, S or N atom; or substituted 5- or 6-membered monocyclic aromatic heterocyclic wherein the heterocyclic bears one halogen, hydroxy, lower alkyl, lower alkylthio, lower alkoxy, cyano or nitro group;
R² and R³ are each hydrogen,
or a physiologically acceptable acid-addition salt thereof.

2. The method of claim 1 wherein R¹ is phenyl, halophenyl or dihalophenyl.

3. The method of claim 1 wherein said compound is in the form of its hydrochloride salt.

4. The method of claim 1 wherein said compound has the name 1-(2,4-dichlorophenyl)-3-(1H-imidazol-1-yl)-2-propen-1-one or its hydrochloride salt.

* * * * *